(12) United States Patent
Canady et al.

(10) Patent No.: US 11,857,242 B2
(45) Date of Patent: Jan. 2, 2024

(54) ATTACHMENT FOR ELECTROSURGICAL SYSTEM

(71) Applicant: U.S. Patent Innovations, LLC, Takoma Park, MD (US)

(72) Inventors: Jerome Canady, Lakeland, FL (US); Feng Yan, Fairfax, VA (US); Taisen Zhuang, Rockville, MD (US); Dereck Chiu, Arlington, VA (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 497 days.

(21) Appl. No.: 16/341,643

(22) PCT Filed: Oct. 31, 2017

(86) PCT No.: PCT/US2017/059384
§ 371 (c)(1),
(2) Date: Apr. 12, 2019

(87) PCT Pub. No.: WO2018/081820
PCT Pub. Date: May 3, 2018

(65) Prior Publication Data
US 2019/0380763 A1    Dec. 19, 2019

Related U.S. Application Data

(60) Provisional application No. 62/415,221, filed on Oct. 31, 2016.

(51) Int. Cl.
*A61B 17/3211* (2006.01)
*A61B 18/12* (2006.01)
(Continued)

(52) U.S. Cl.
CPC ........ *A61B 18/042* (2013.01); *A61B 17/3211* (2013.01); *A61B 18/1206* (2013.01);
(Continued)

(58) Field of Classification Search
CPC ............ A61B 18/1206; A61B 17/3211; A61B 2018/00178; A61B 2018/00595;
(Continued)

(56) References Cited

U.S. PATENT DOCUMENTS 4,040,426 A    8/1977  Morrison
4,429,694 A    2/1984  McGreevy
(Continued)

FOREIGN PATENT DOCUMENTS

JP    2007510519 A    4/2007
JP    2016013451 A    1/2016
(Continued)

OTHER PUBLICATIONS

A. Erwine, "ESU-2000 Series Product Overview A Paradigm Shift in Electrosurgery Testing Technology and Capability Is Here," BC Group International, Inc. (2007).

*Primary Examiner* — Joseph A Stoklosa
*Assistant Examiner* — Annie L Shoulders
(74) *Attorney, Agent, or Firm* — 24IP Law Group USA, PLLC; Timothy R DeWitt

(57) ABSTRACT

An attachment for a gas-assisted electrosurgical device. The attachment has a housing having a channel within it, an electrosurgical blade and an electrical connector. The electrosurgical blade has a conductive member comprising an elongated distal portion and a proximal portion, the distal portion having a width greater than a width of the proximal portion, the width of the distal portion being at least three times the thickness of the distal portion, and a coating on at least a portion of said conductive member.

11 Claims, 18 Drawing Sheets

(51) Int. Cl.
  *A61B 18/00* (2006.01)
  *A61B 18/14* (2006.01)
  *A61B 18/04* (2006.01)

(52) U.S. Cl.
  CPC ............... *A61B 2018/00178* (2013.01); *A61B 2018/00589* (2013.01); *A61B 2018/00595* (2013.01); *A61B 2018/00601* (2013.01); *A61B 2018/1412* (2013.01)

(58) Field of Classification Search
  CPC ........... A61B 2018/00589; A61B 2018/00601; A61B 298/1412
  See application file for complete search history.

(56) References Cited

U.S. PATENT DOCUMENTS

| | | | |
|---|---|---|---|
| 4,754,754 A * | 7/1988 | Garito | A61B 17/3213 606/49 |
| 4,781,175 A | 11/1988 | McGreevy et al. | |
| 5,088,997 A | 2/1992 | Delahuerga et al. | |
| 5,207,675 A | 5/1993 | Canady | |
| 5,217,457 A | 6/1993 | Delahuerga et al. | |
| 5,951,551 A | 9/1999 | Erlich | |
| 6,610,057 B1 | 8/2003 | Ellman et al. | |
| 7,066,936 B2 | 6/2006 | Ryan | |
| 7,147,634 B2 | 12/2006 | Nesbitt | |
| 7,288,091 B2 | 10/2007 | Nesbitt | |
| 7,390,326 B2 | 6/2008 | Nesbitt | |
| 2005/0154385 A1 | 7/2005 | Heim et al. | |
| 2007/0093811 A1 * | 4/2007 | Nesbitt | A61B 18/1402 606/45 |
| 2012/0221002 A1 * | 8/2012 | Long | A61B 34/76 606/45 |
| 2013/0296848 A1 | 11/2013 | Allen et al. | |
| 2016/0095644 A1 * | 4/2016 | Canady | A61B 18/042 606/45 |

FOREIGN PATENT DOCUMENTS

| | | | | |
|---|---|---|---|---|
| WO | 2015/164676 A1 | 10/2015 | | |
| WO | WO-2015164676 A1 * | 10/2015 | ........... | A61B 18/042 |

* cited by examiner

ATTACHMENT FOR ELECTROSURGICAL SYSTEM

CROSS-REFERENCE TO RELATED APPLICATIONS

The present application claims the benefit of the filing date of U.S. Provisional Patent Application Ser. No. 62/415,221 filed by the present inventors on Oct. 31, 2016.

The present application further is related to U.S. Patent Application Publication No. 2016/0051313 entitled "Attachment For Electrosurgical System," U.S. Patent Application Publication No. 2016/0095644 entitled "Cold Plasma Scalpel, and WO 2015/164676 entitled "Multi-Functional Electrosurgical Plasma Accessory," all of which are hereby incorporated by reference in their entirety.

BACKGROUND OF THE INVENTION

Field of the Invention

The present invention relates to electrosurgical systems and methods, and more particularly, to electrodes for gas-assisted electrosurgical systems and methods.

Brief Description of the Related Art

The standard means for controlling traumatic and surgical blood loss are electrosurgical generators and lasers which respectively direct high-frequency electrical current or light energy to localize heat in bleeding vessels so as to coagulate the overlying blood and vessel walls. Hemostasis and tissue destruction are of critical importance when removing abnormal tissue during surgery and therapeutic endoscopy. For monopolar electrosurgery electrical energy originates from an electrosurgical generator and is applied to target tissue via an active electrode that typically has a small cross-sectional surface-area to concentrate electrical energy at the surgical site. An inactive return electrode or patient plate that is large relative to the active electrode contacts the patient at a location remote from the surgical site to complete and electrical circuit through the tissue. For bipolar electrosurgery, a pair of active electrodes are used and electrical energy flows directly through the tissue between the two active electrodes.

U.S. Pat. No. 4,429,694 to McGreevy disclosed a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and by McGreevy in U.S. Pat. No. 4,781,175. This method, referred to as argon plasma coagulation (APC) or argon beam coagulation (ABC) is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

APC has been demonstrated to be effective in the coagulation of blood vessels and human tissue during surgery. APC functions in a noncontact manner. The electrical current is initiated only when the tip of the handpiece or catheter is within one centimeter of the target tissue and produces a homogenous 1 mm to 2 mm well-delineated eschar. The eschar created by APC is further characterized by a decrease absence of charring and carbonization compare to eschar resulting from conventional electrosurgical fulguration. The eschar remains firmly attached to the tissue, in contrast to other coagulation modalities where there is an overlying charred layer of coagulated blood. There is minimal tissue necrosis with APC.

In U.S. Pat. Nos. 5,217,457 and 5,088,997 to Delahuerga et al. disclosed a device for performing procedure referred to as "argon shrouded cut." The device was an electrosurgical pencil having an exposed electrode with a distal end defining a tip for cutting biological tissue and a nose piece mounted about the electrode to define a pathway for a stream of inert gas which shrouds the electrode at or near its tip. When in coagulation mode, a convergent stream of inert gas was directed directly onto the tip of the electrode. In coagulation mode, the voltage was sufficient to initiate an electrical discharge in the inert gas. In cut mode, the stream of ionized gas was directed to impinge obliquely on the electrode at a point adjacent to but away from the tip of the electrode. In cutting mode, the open circuit voltage was generally not high enough to continuously plasmatize the inert gas and initiate and maintain an electrical discharge. Accordingly, in cut mode the function of the inert gas is to provide a shroud around the electrode rather than to initiate electrical discharge.

A multitude of literature exists that discloses and discusses various commercially available electrosurgical generators and the voltage waveforms produced by those generators. For example, A. Erwine, "ESU-2000 Series Product Overview A Paradigm Shift in Electrosurgery Testing Technology and Capability Is Here," BC Group International, Inc. (2007) describes electrosurgical generators from ERBE Elektromedizin GmbH and ConMed Corporation, among others.

In U.S. Patent Application Publication No. US-2013-0296848, Canady et al. described electrosurgical systems and methods using argon plasma during cutting modes of operation. The disclosed electrosurgical device had a handpiece or pencil having a rigid housing and telescoping nozzle or tip. The rigid housing may be formed, for example, from molded sides. The two sides are joined to form housing having a hollow chamber within. Within the housing is a needle electrode, electrode tubing and a fiberglass plate. The needle electrode extends through the electrode tubing. The electrode tubing additional has within it a channel, tube or other means for conducting the inert gas from the distal end of tubing through the electrode tubing and out of the electrode tubing. The inert gas leaving the channel in the electrode tubing then passes out of an opening at the distal end of the nozzle. The fiberglass plate and electrode are connected to electrical cable assembly. The electrode tubing is connected at its distal end to the PVC hose tubing. An O-ring is placed between the telescoping nozzle and the electrode tubing to form a seal there between. A ceramic tip may be placed at a distal end of the telescoping tip or nozzle to protect the nozzle from heat damage where the electrode passes through an opening at the distal end of the nozzle.

The electrical cable assembly extends from a proximal end of the housing and has at its distal end a plug. During operation of the device, the connector is connected to an electrosurgical generator. The PVC hose tubing also extends from the proximal end of the housing and has at its distal end a gas connector body, a gas connector tip and an O-ring. During operation of the device, the gas connector assembly is connected to a source of an inert gas such as argon. The housing has a plurality of opening or holes for accommodating a plurality of controls or buttons. The telescoping nozzle or tip has a control element extending through a slot in the housing. The control element, tab, know or slider is used by a surgeon to move the telescoping tip into or out of an opening in a distal end of the housing. Three controls or buttons extend out of openings in the housing and have springs between them and fiberglass plate to bias the controls or buttons away from the plate or connector.

The electrosurgical device of U.S. Patent Application Publication No. US-2013-0296848 could be operated, for example, in four different modes: conventional cut mode, conventional coagulation mode, argon plasma coagulation mode, and hybrid plasma cut mode. The eschar resulting from cutting and coagulation in the hybrid plasma cut mode in accordance with the present invention is substantially better than conventional fulguration, cutting and argon plasma coagulation techniques. In addition there is substantial absence of charring, carbonization, tissue necrosis and destruction of adjacent tissue. Thus, tissue can be precisely cut and the adjacent vessels simultaneously sealed with minimal depth of injury, tissue necrosis, eschar and carbonization.

Any generator that provides high-frequency voltage to ionize the inert gas to form a gas stream can be used. Preferred generators include the Canady Plasma™ Electrosurgery Unit model (SS-601 MCa) and the Canady Plasma™ Electrosurgery Unit model (SS-200E) that are preferably used with the Argon plasma units Canady Plasma™ Argon 4 Coagulator (CPC 4) and Canady Plasma™ Argon 2 Coagulator (CPC 2), respectively. The CPC 4 provides a controlled flow of inert gas to the electrosurgical device during argon plasma coagulation mode and in hybrid plasma cut mode. The flow rate and the power can be manually set. In a coagulation mode, the generator delivers, for example, a peak-to-peak voltage of less than 9000 volts. In a cut mode, for example, the generator delivers a peak-to-peak voltage of less than 3800 volts. Most preferably, a peak-to-peak voltage of 100 to 9000 volts is delivered by the generator. Any accessory devices could be attached to the electrosurgical unit/plasma unit combination. Exemplary devices are an electrosurgical device (a handpiece) or an argon plasma flexible probe (catheter), rigid or laparoscopic.

For operating the electrosurgical device disclosed in U.S. Patent Application Publication No. US-2013-0296848, high-frequency current can be activated by two push buttons for the conventional cut mode and the conventional coagulation mode, respectively. Argon gas may be delivered by activating a third push button. This activation will allow the argon plasma coagulation mode and the hybrid plasma cut mode. The plasma cut mode will cut and coagulate the tissue at the same time. It can be easily switched between the different modes by activating the respective buttons. The plasma or electrical current can also be activated by a footswitch.

In U.S. Patent Application Publication No. US-2013-0296848, the electrosurgical scalpel took the form of a needle or wire. Such a form is common with conventional electrosurgical staplers. Electrosurgical scalpels, however, can take many other forms, for example, as shown in U.S. Pat. No. 7,066,936 to Ryan, U.S. Pat. No. 6,610,057 to Ellman et al., U.S. Pat. No. 5,951,551 to Erlich.

SUMMARY OF THE INVENTION

In a preferred embodiment, the present invention is an attachment for a gas-assisted electrosurgical device. The attachment comprises a housing, a channel within said housing, a connector for connecting said channel to a gas source, an electrosurgical scalpel or blade and a connector for connecting said electrosurgical scalpel to an electrosurgical generator. The electrosurgical scalpel or blade is elongated and has a proximal portion or step portion that may be round like a wire or may be flat and a flat or paddle-like distal portion. In the flat or paddle-like distal portion the width of the scalpel or blade is approximately 4 times the thickness of the blade and the distal end is rounded or curved. The thickness of the distal paddle-like portion is preferably in the range of 0.49 mm-0.55 mm while the width preferably is 2.19 mm-2.25 mm. Preferably the blade is made of stainless steel with a surface coating preferably of ElectroBond™ from Surface Solutions Group, LLC. Information regarding such coatings is disclosed in U.S. Pat. Nos. 7,390,326, 7,288,091, 7,147,634.

In another preferred embodiment, the present invention is an attachment for a gas-assisted electrosurgical device. The attachment comprising an assembly having an elongated housing, an electrosurgical blade within the housing, and a conductive connector at a proximal end of the housing and connected to a proximal end of the conductive member. The elongated housing comprises an elongated body having a channel within it and a proximal portion having a plurality of arms extending therefrom with each of the plurality of arms having an outward extending flange. The electrosurgical blade comprises a conductive member comprising an flat distal portion and an elongated proximal portion, the flat distal portion having a width greater than a width of the proximal portion, the width of the distal portion being at least three times a thickness of the distal portion and a coating on at least a portion of the conductive member. The connector, which connects the electrosurgical blade to an electrosurgical generator, comprises a body, a channel within the body, an opening for receiving the proximal portion of the conductive member wherein a proximal end of the conductive member is secured in the opening. The conductive member may comprise, for example, one of stainless steel and tungsten. The assembly may further comprise a ceramic tip at a distal end of the housing, wherein the ceramic tip surrounds part of the distal portion of the conductive member and the ceramic tip has a proximal portion within the channel in the housing and a distal portion extending out of the channel in the housing. The distal portion of the conductive member has a rounded tip. The assembly may further comprise a support member within the channel in the housing body for supporting the conductive member within the housing. The assembly may further comprise a connector for connecting the assembly to an electrosurgical hand piece. The connector body may have a flat side for aligning the connector with the housing. The body of the connector may be cylindrical in form and the opening for receiving the proximal end of the conductive member is off center in the cylindrical connector body. The channel in the conductive body runs along a central axis of conductor body. The width of the distal portion of the conductive member may be parallel to the flat side of the connector for aligning the conductive member in the channel in the housing.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

The attachment for a gas-assisted electrosurgical system of the present invention has a housing 100, a channel within the housing, a connector (not shown) for connecting said channel to a gas source (not shown), an electrosurgical scalpel or blade 200 and a connector 500 for connecting said electrosurgical scalpel to an electrosurgical generator (not shown).

Figure 1A:
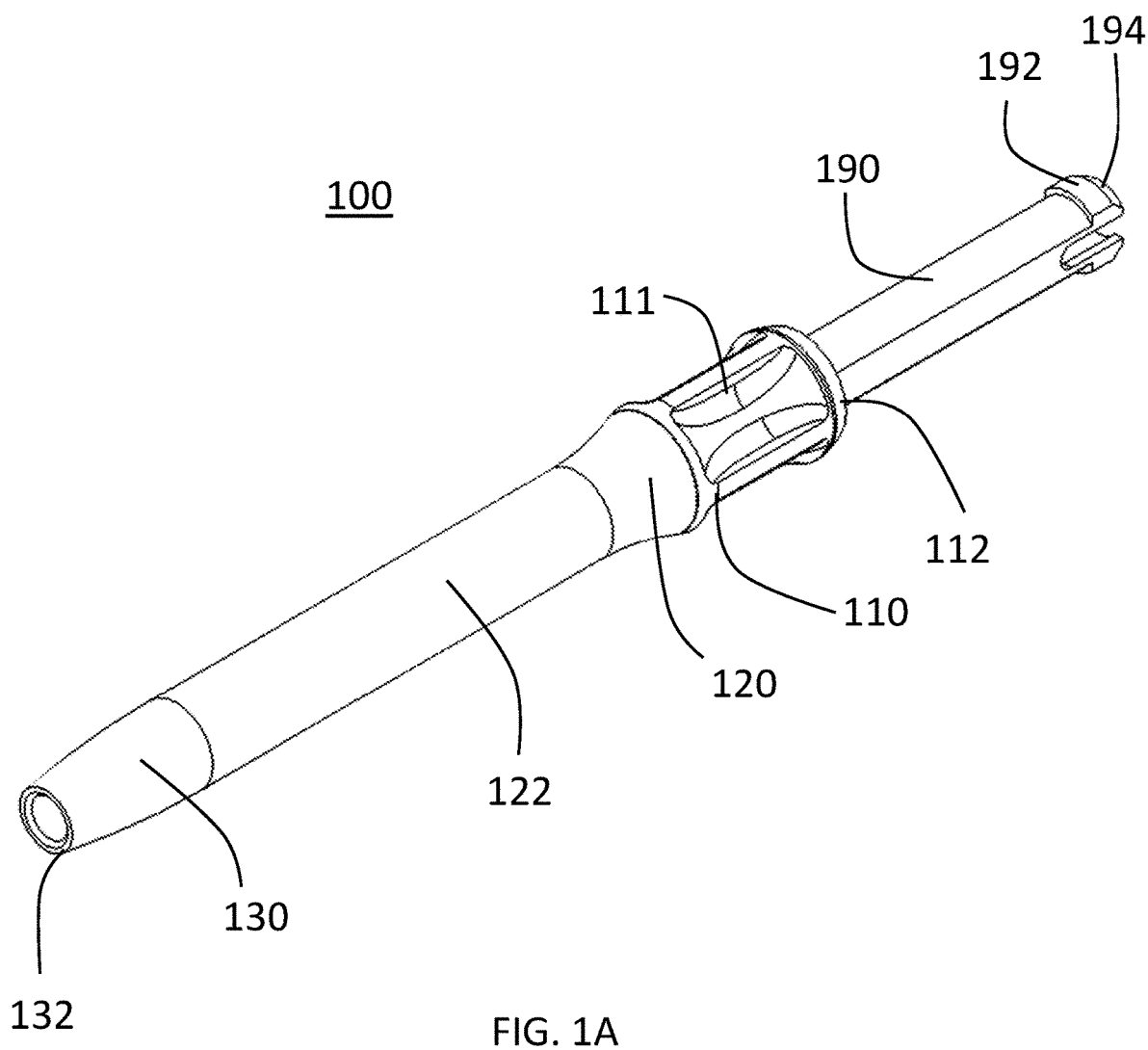
FIG. 1A is a perspective view of a housing for an electrosurgical blade in accordance with a preferred embodiment of the present invention.
Figure 1B:
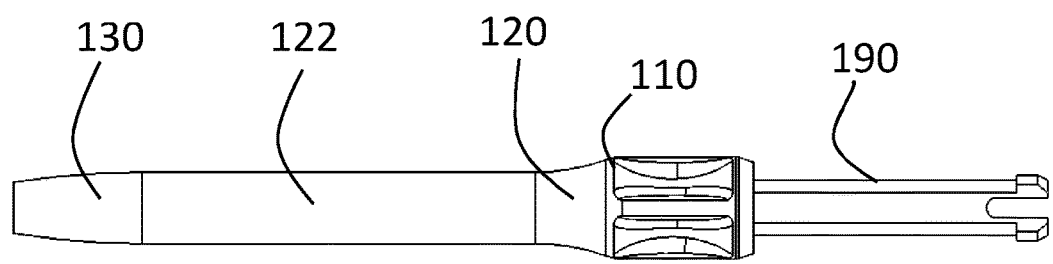
FIG. 1B is a first side view of a housing for an electrosurgical blade in accordance with a preferred embodiment of the present invention.
Figure 1C:
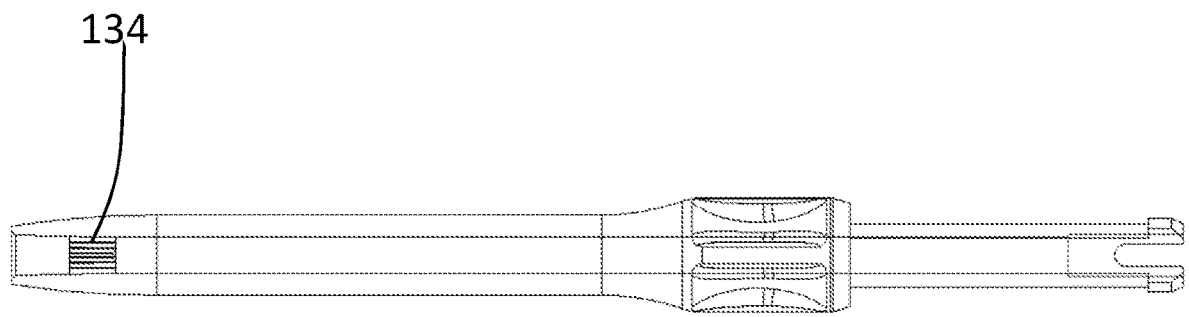
FIG. 1C is a sectional first side view of a housing for an electrosurgical blade in accordance with a preferred embodiment of the present invention.
Figure 1D:
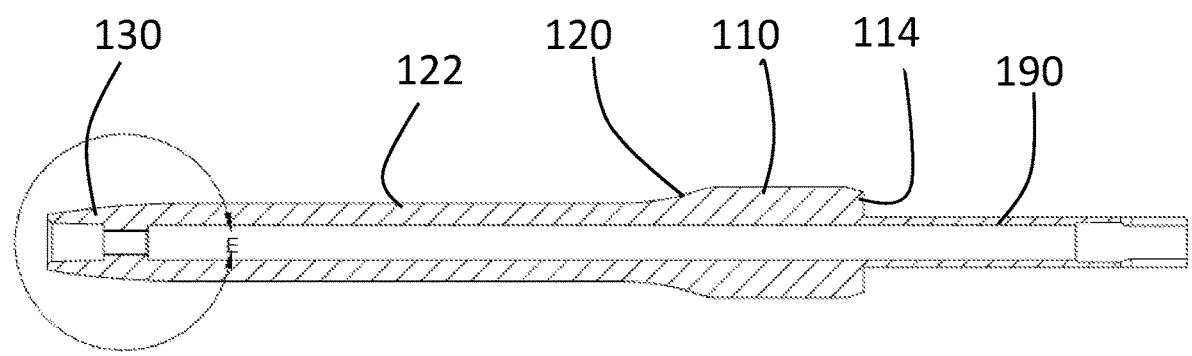
FIG. 1D is a cross-sectional view of a housing for an electrosurgical blade in accordance with a preferred embodiment of the present invention.
Figure 1E:
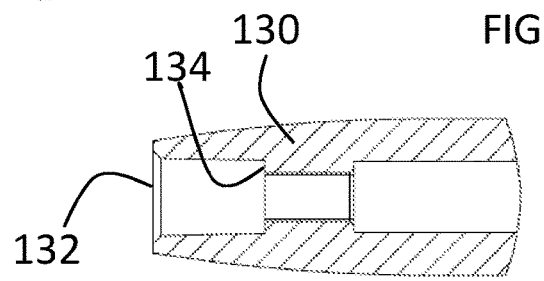
FIG. 1E is an enlarged portion of the cross-sectional view of FIG. 2D of a housing for an electrosurgical blade in accordance with a preferred embodiment of the present invention.
Figure 1F:
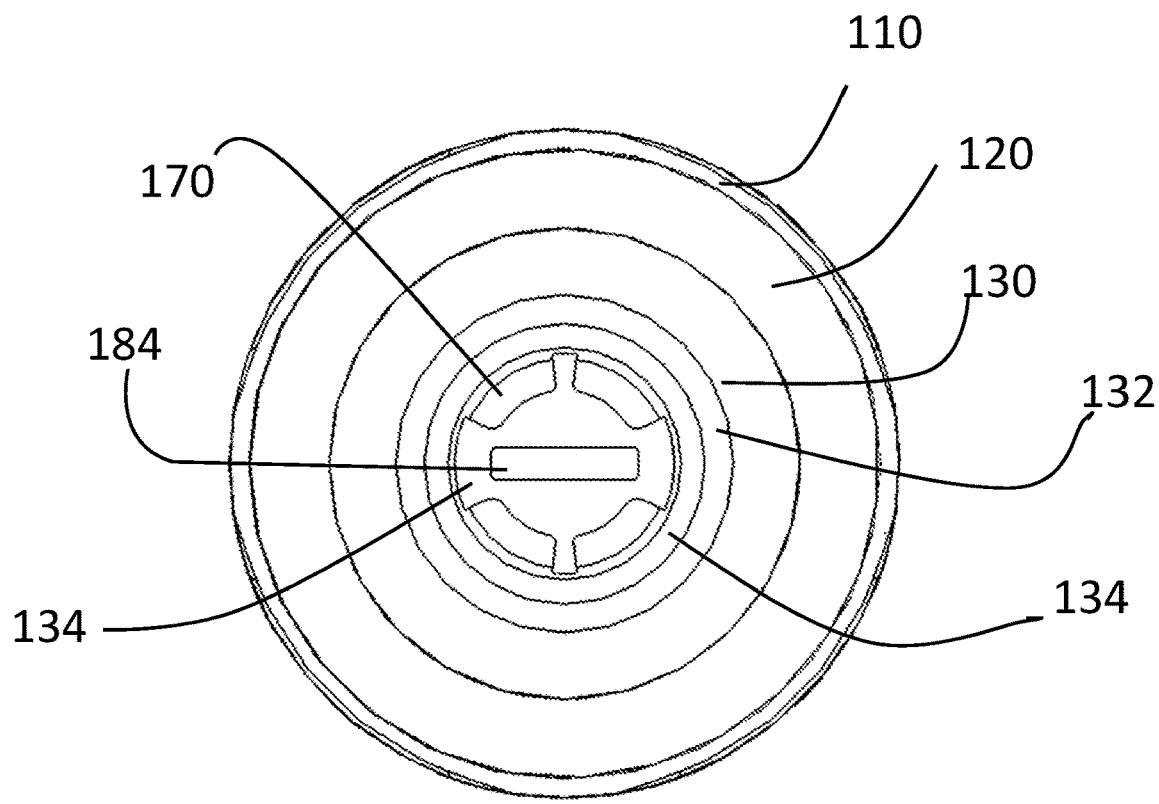
FIG. 1F is a distal end view of a housing for an electrosurgical blade in accordance with a preferred embodiment of the present invention.
Figure 1G:
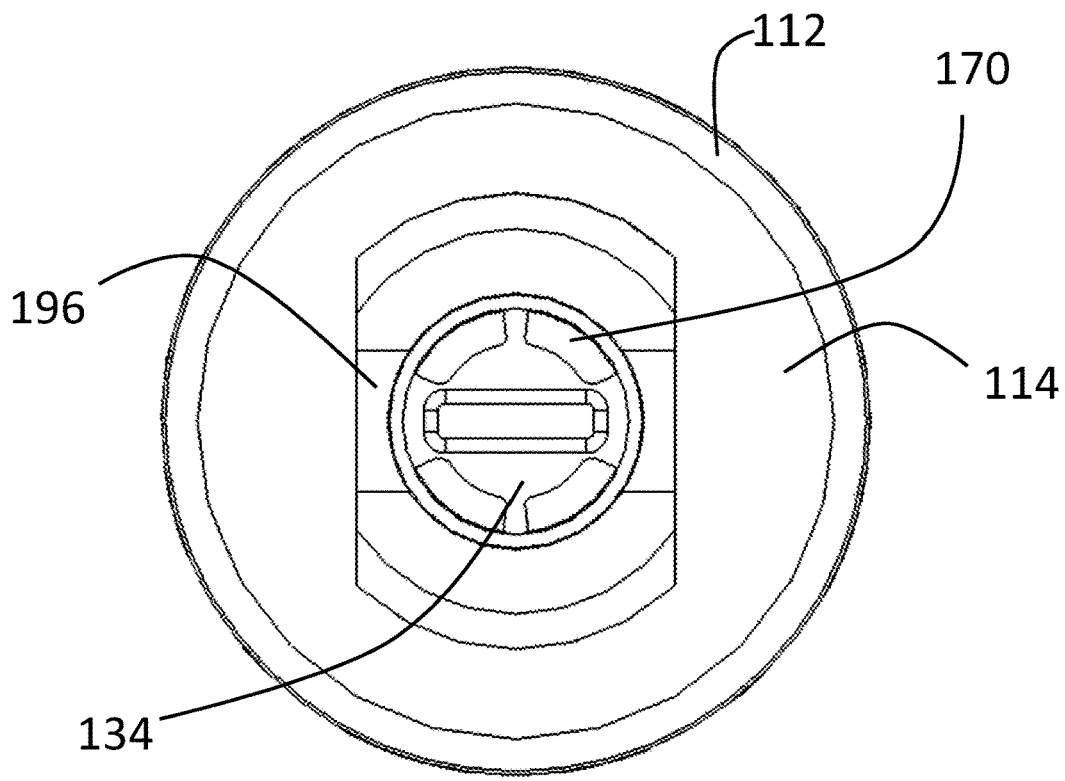
FIG. 1G is a proximal end view of a housing for an electrosurgical blade in accordance with a preferred embodiment of the present invention.
Figure 1H:
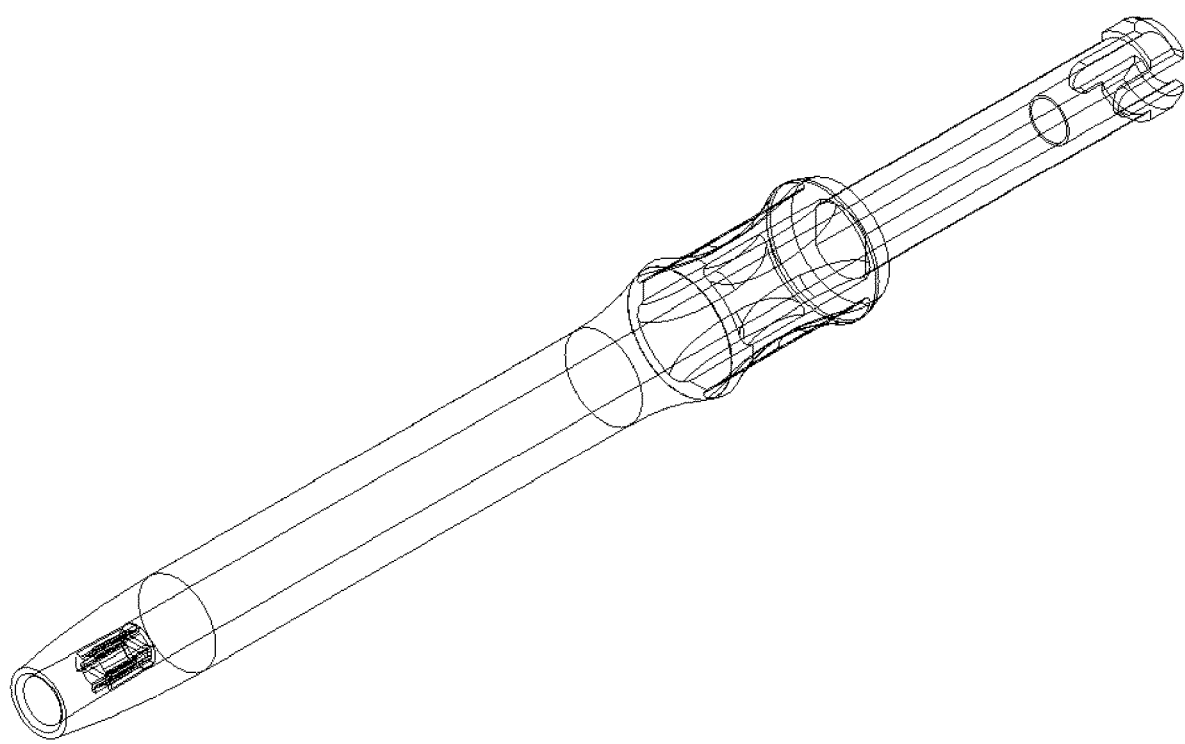
FIG. 1H is a perspective x-ray view of a housing for an electrosurgical blade in accordance with a preferred embodiment of the present invention.

A housing 100 for an electrosurgical blade in accordance with a preferred embodiment of the present invention is shown in FIGS. 1A-1H. The housing 100 has a plurality of section 110, 120, 122, and 190, for example, made of plastic, channel 170 that runs along the length of the housing 100 and a nozzle or tip 130. The sections 110, 120, 122 and 190 may be separate parts, may be telescoping in part or in whole, or may be formed as an integral part such as by molding. The nozzle or tip 130 has a beveled edge 132 at its distal end. Further, there may be a ceramic tip 134 inside and/or extending from said nozzle or tip 130. The portion 110 has structural members such as ridges or grooves 111 for facilitating gripping of the housing by a user's hand, a beveled proximal end 112, and a shoulder 114. The proximal portion 190 of the housing 100 has a plurality of flanges 192 having beveled edges 194 for connecting the housing to an electrosurgical hand piece.

The housing 100 further has a spacer or support 134 inside the channel 170 for supporting and electrode. The spacer 134 has a plurality of openings into the channel 170 and an opening 184 for receiving an electrode.

Figure 2A:
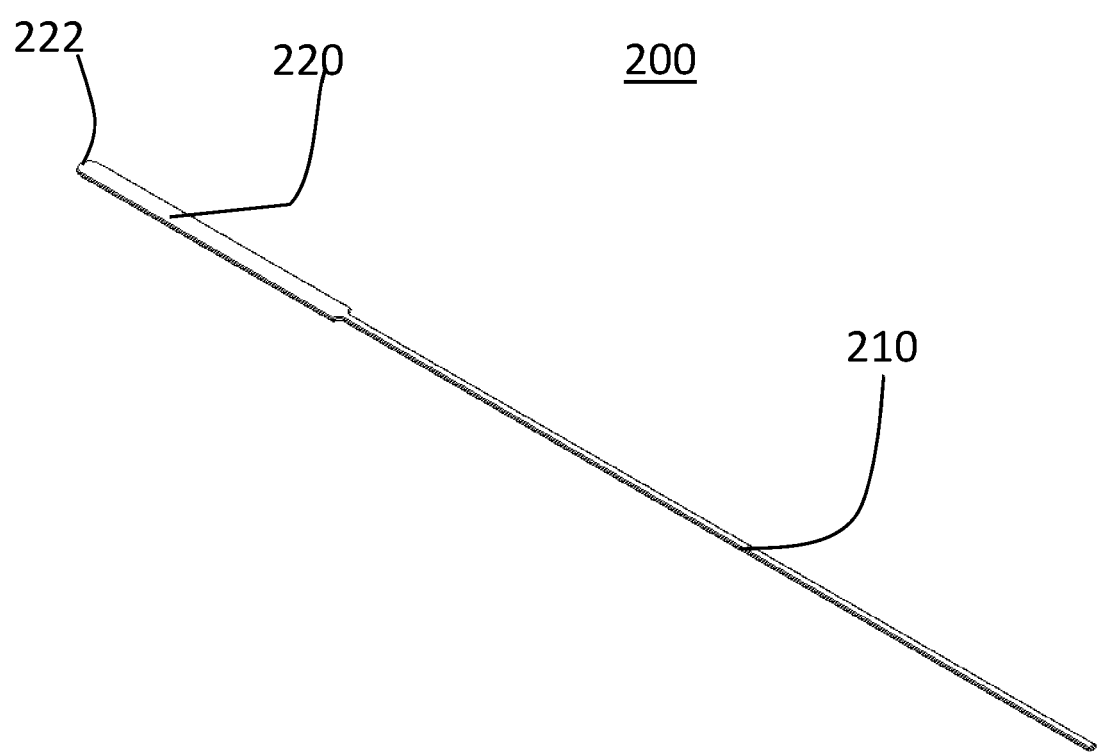
FIG. 2A is a perspective view of an electrosurgical surgical blade in accordance with a preferred embodiment of the present invention.
Figure 2B:
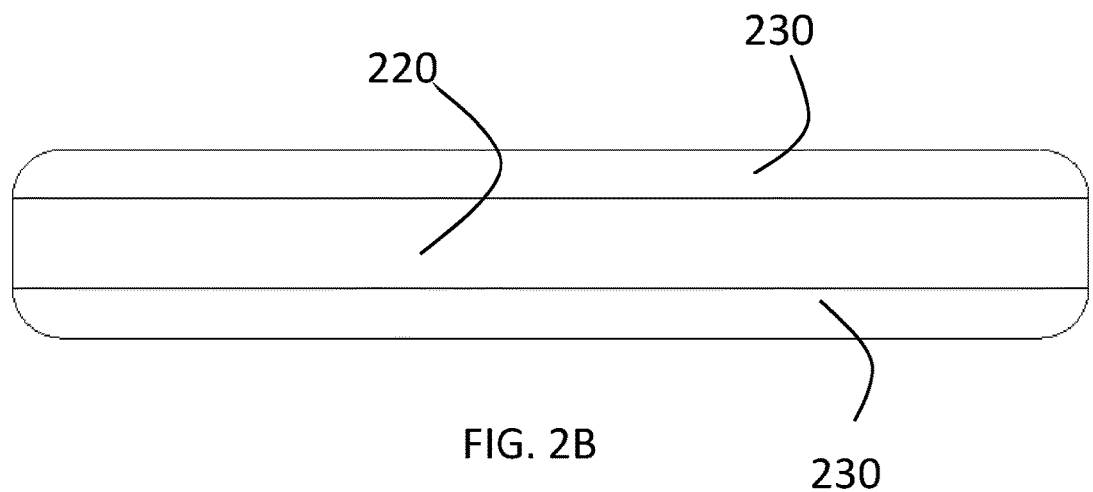
FIG. 2B is a distal end of an electrosurgical surgical blade in accordance with a preferred embodiment of the view present invention.
Figure 2C:
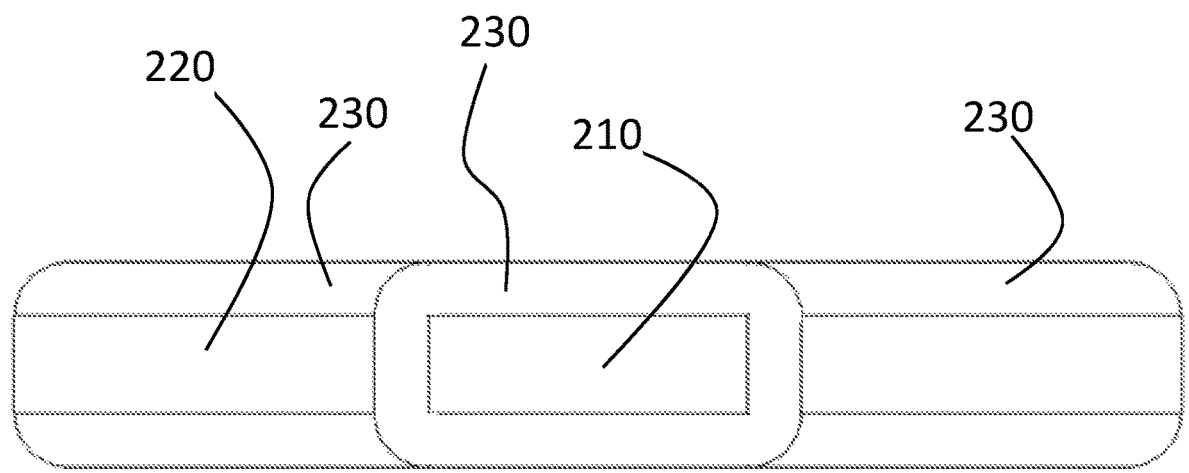
FIG. 2C is a proximal end view of an electrosurgical surgical blade in accordance with a preferred embodiment of the present invention.
Figure 2D:
FIG. 2D is a side view of an electrosurgical surgical blade in accordance with a preferred embodiment of the present invention.

A surgical blade in accordance with a preferred embodiment of the present invention is shown in FIGS. 2A-2D. The electrosurgical scalpel or blade 200 is elongated and has a proximal portion 210 that may be round like a wire or may be flat and a flat or paddle-like distal portion 220. The flat or paddle-like distal portion 220 has a width at least four times its thickness. Tip 222 of the distal blade portion 220 is rounded or curved. The thickness of the distal paddle-like portion 220 is preferably in the range of 0.49 mm-0.55 mm while the width preferably is 2.19 mm-2.25 mm. Preferably the blade 200 is made of stainless steel with a surface coating 230 preferably of ElectroBond™ from Surface Solutions Group, LLC. Information regarding such coatings is disclosed in U.S. Pat. Nos. 7,390,326, 7,288,091, 7,147,634.

Figure 3A:
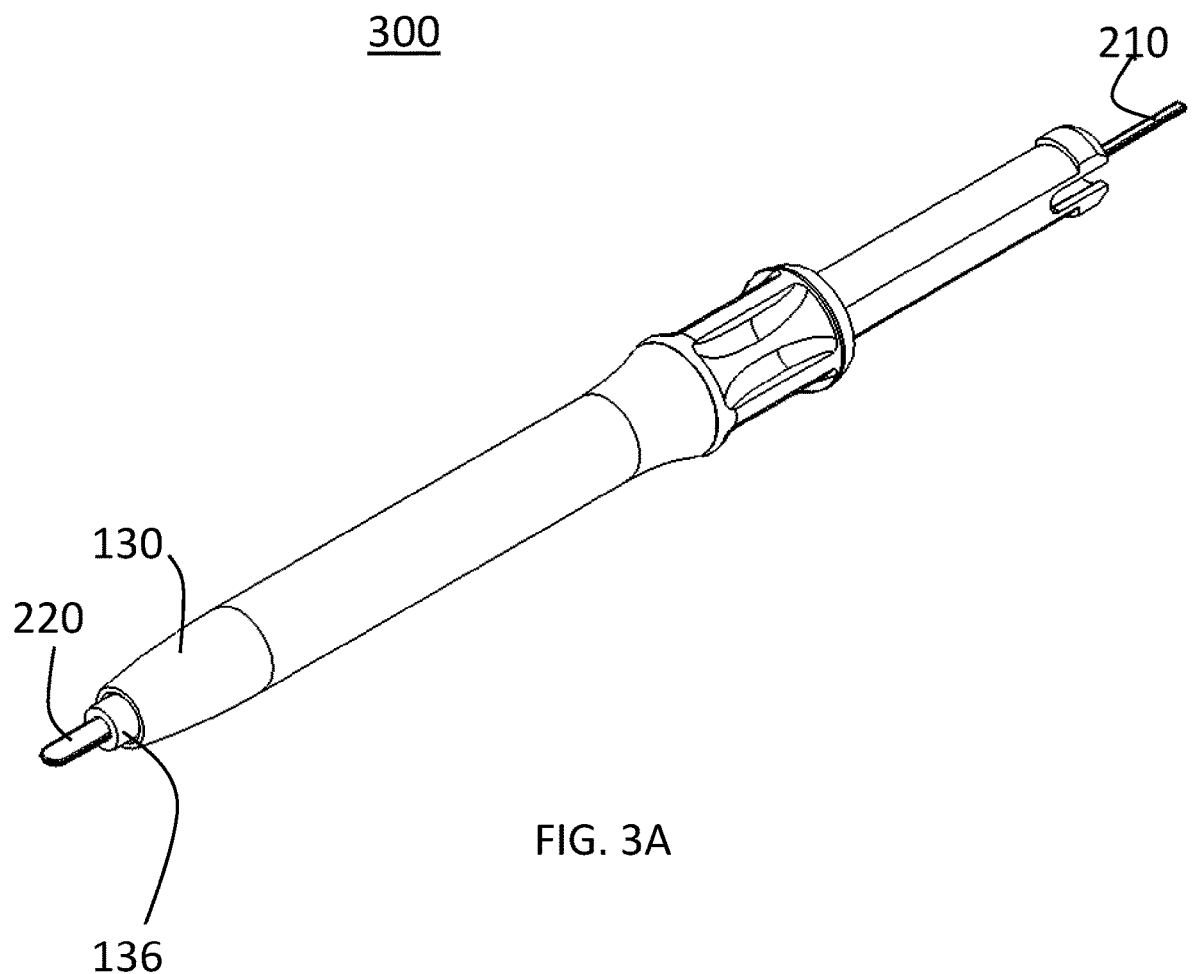
FIG. 3A is a perspective view of an electrosurgical surgical blade and housing assembly in accordance with a preferred embodiment of the present invention.
Figure 3B:
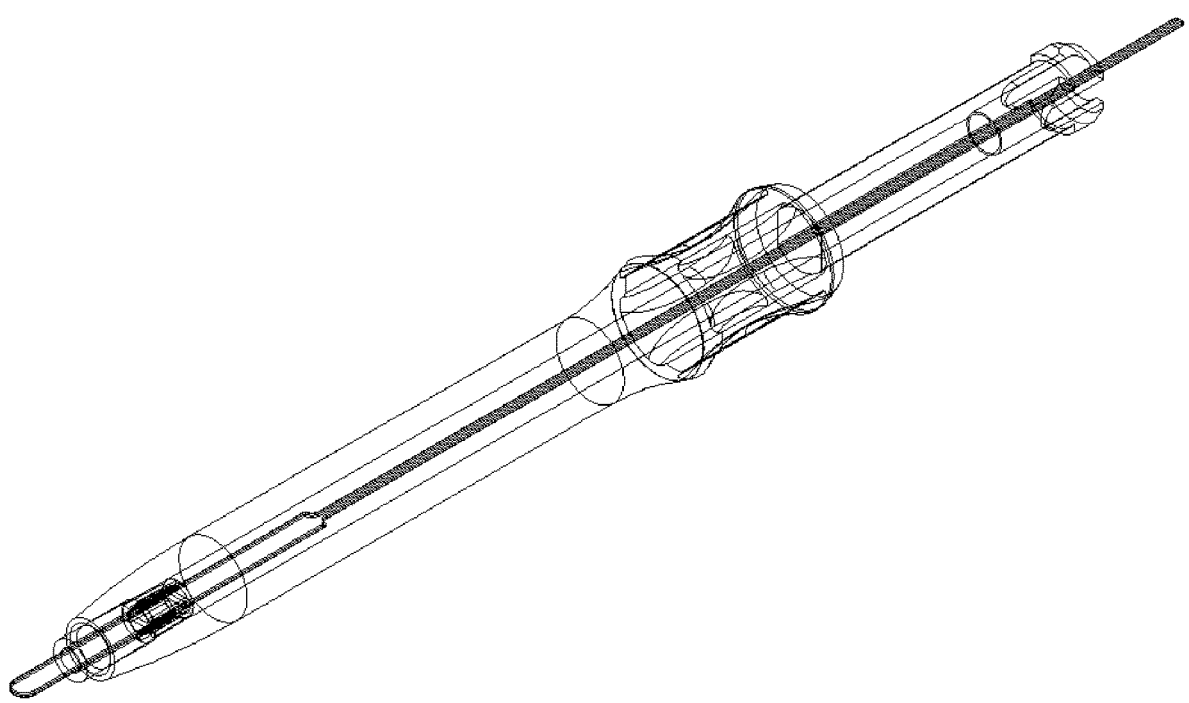
FIG. 3B is an X-ray perspective view of an electrosurgical surgical blade and housing assembly in accordance with a preferred embodiment of the present invention.
Figure 3C:
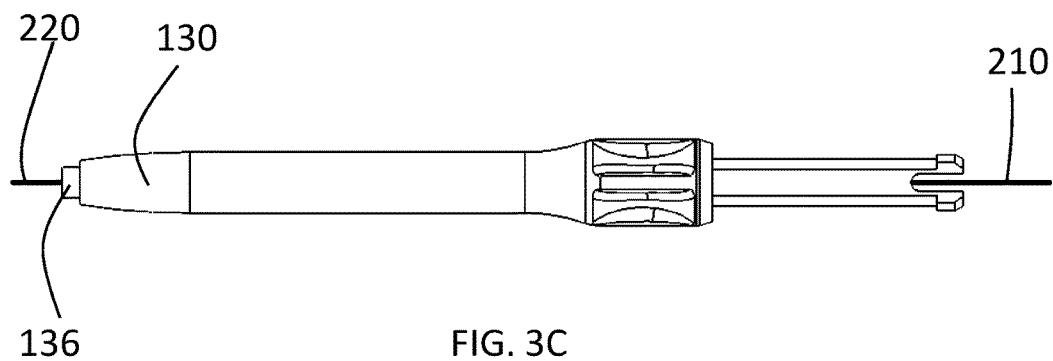
FIG. 3C is a first side view of an electrosurgical surgical blade and housing assembly in accordance with a preferred embodiment of the present invention.
Figure 3D:
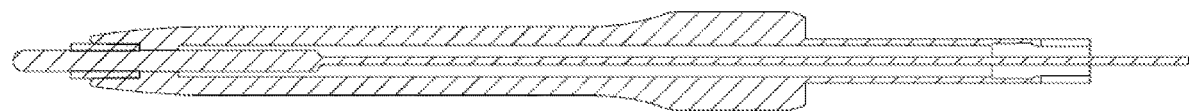
FIG. 3D is a cross-sectional side view of an electrosurgical surgical blade and housing assembly in accordance with a preferred embodiment of the present invention.
Figure 3E:
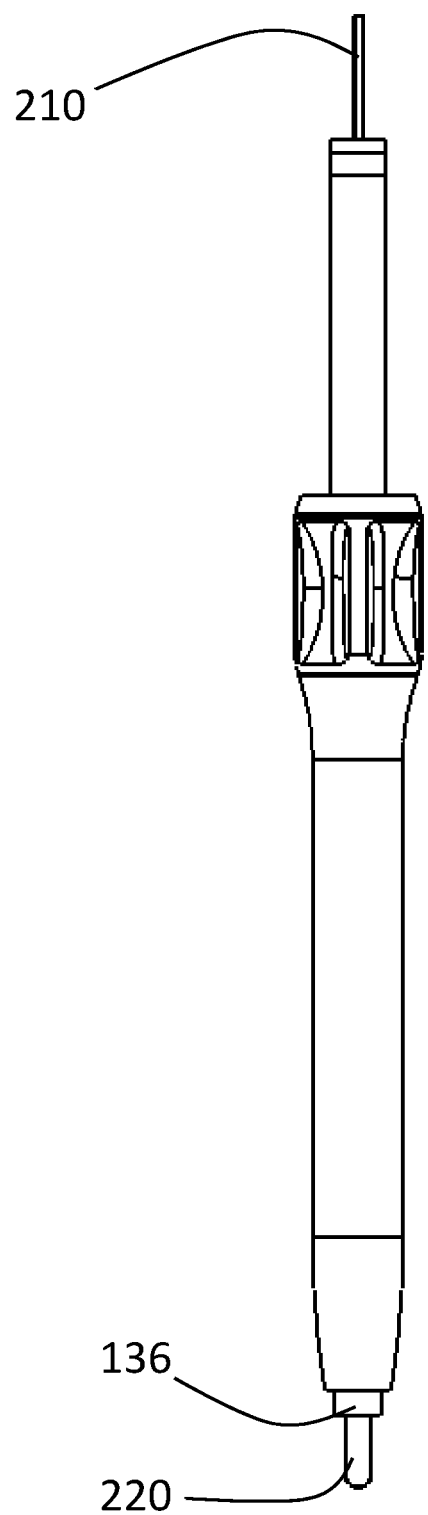
FIG. 3E is a second side view of an electrosurgical surgical blade and housing assembly in accordance with a preferred embodiment of the present invention.
Figure 3F:
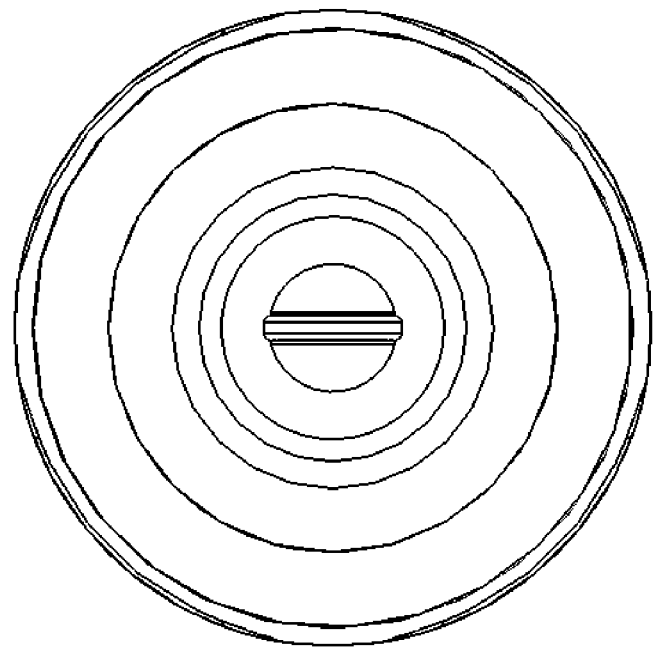
FIG. 3F is a distal end view of an electrosurgical surgical blade and housing assembly in accordance with a preferred embodiment of the present invention.
Figure 3G:
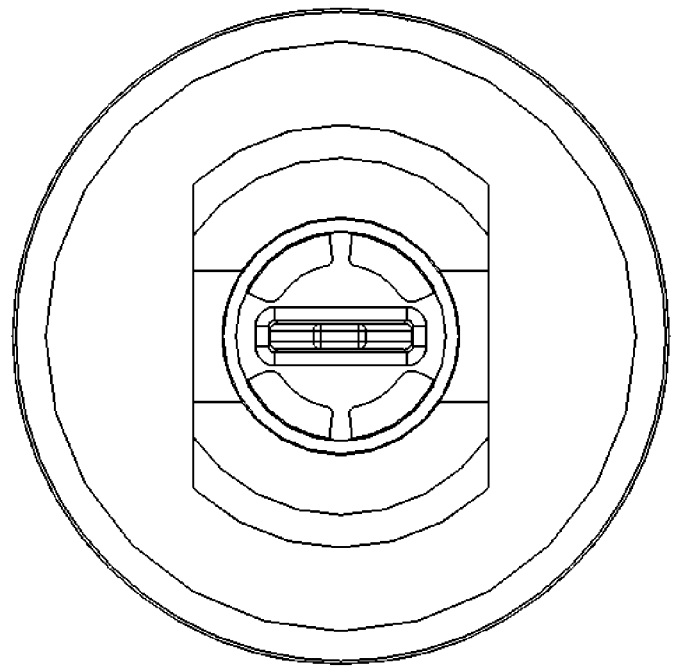
FIG. 3G is a proximal end view of an electrosurgical surgical blade and housing assembly in accordance with a preferred embodiment of the present invention.

An assembly of a surgical blade 200 within a housing 100 in accordance with a preferred embodiment of the present invention is shown in FIGS. 3A-3G. The surgical blade, which is an electrode, is inserted into the distal end of the tubing, housing or body 100.

When the attachment 300 is assembled, blade 200 extends down approximately the center of the channel in the housing 100 to a position near or extending from the distal end of the housing 100 and the tip 130. The ceramic tip 136 surrounds the blade near the nozzle or tip 130 and may be inside the nozzle 130 and/or may extend outside the nozzle 130.

Figure 4A:
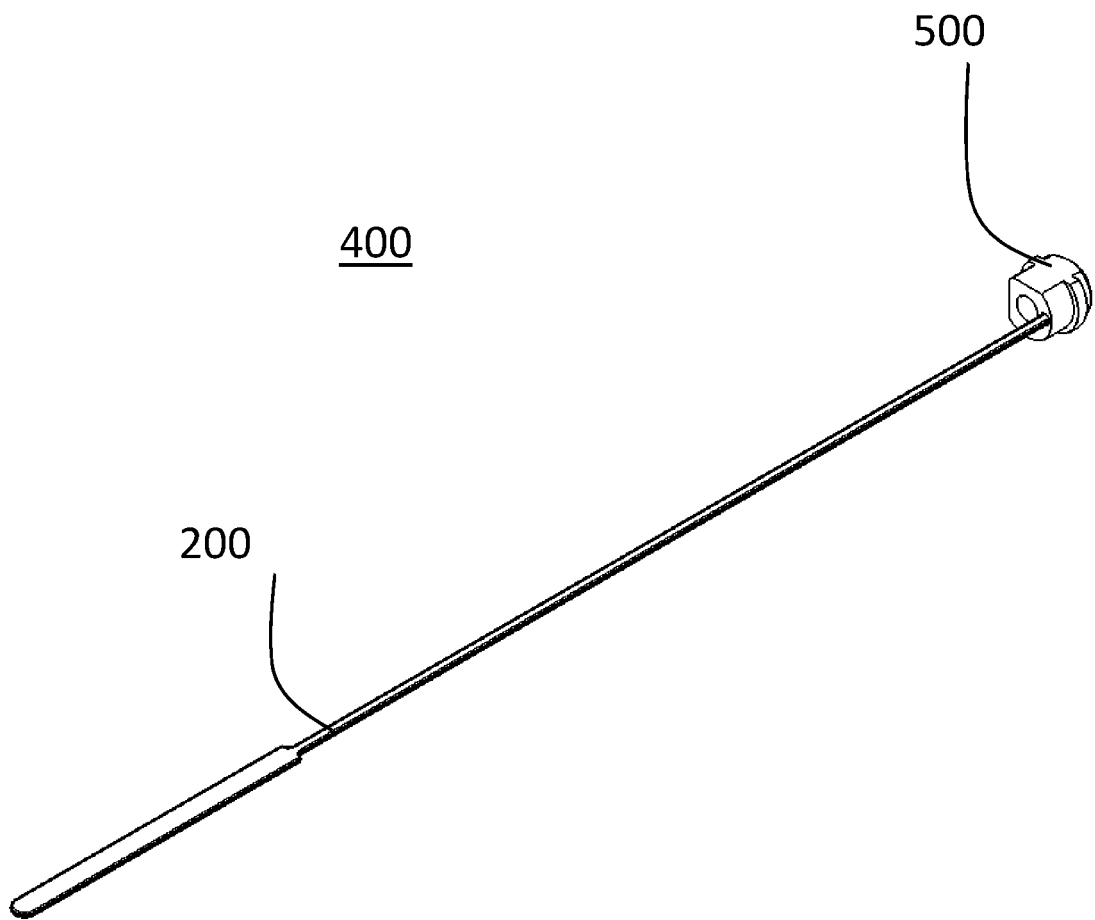
FIG. 4A is a perspective view of an electrosurgical surgical blade and connector assembly in accordance with a preferred embodiment of the present invention.
Figure 4B:
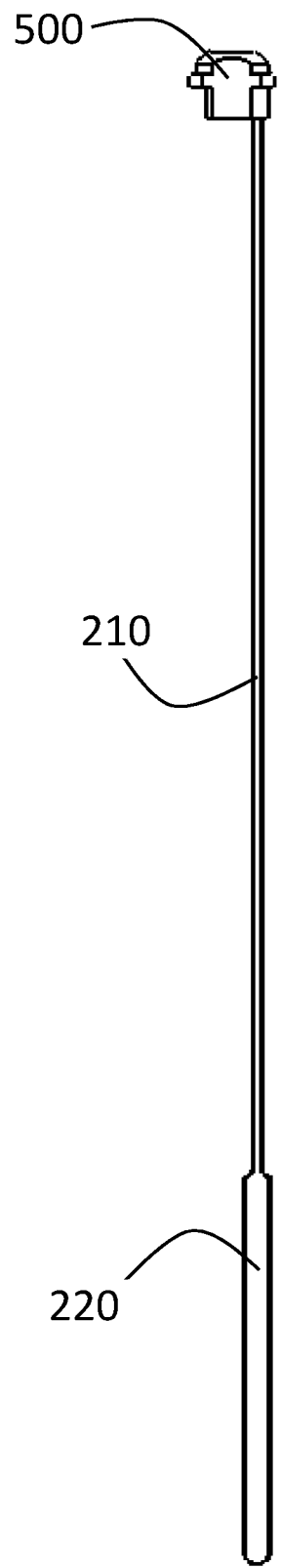
FIG. 4B is a first side view of an electrosurgical surgical blade and connector assembly in accordance with a preferred embodiment of the present invention.
Figure 4C:
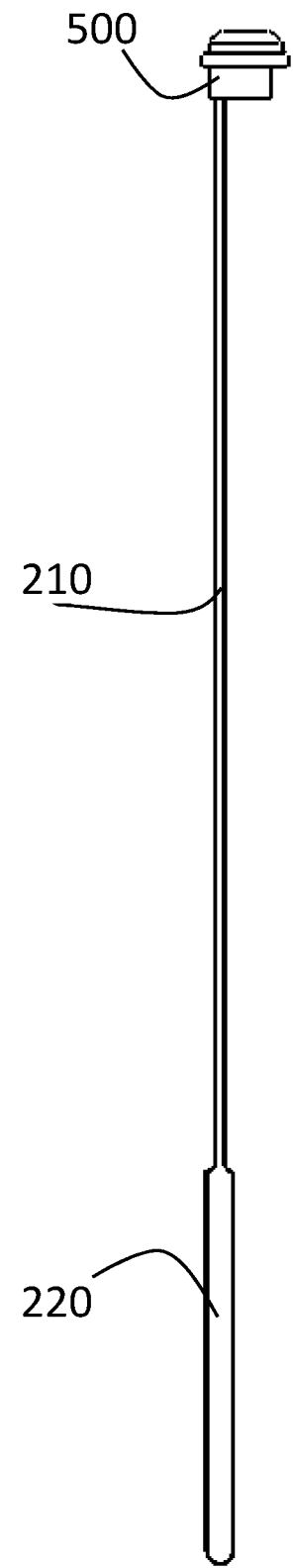
FIG. 4C is a second side view of an electrosurgical surgical blade and connector assembly in accordance with a preferred embodiment of the present invention.
Figure 4D:
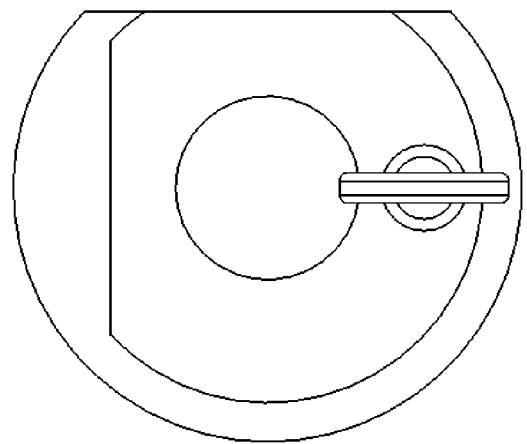
FIG. 4D is a distal end view of an electrosurgical surgical blade and connector assembly in accordance with a preferred embodiment of the present invention.
Figure 4E:
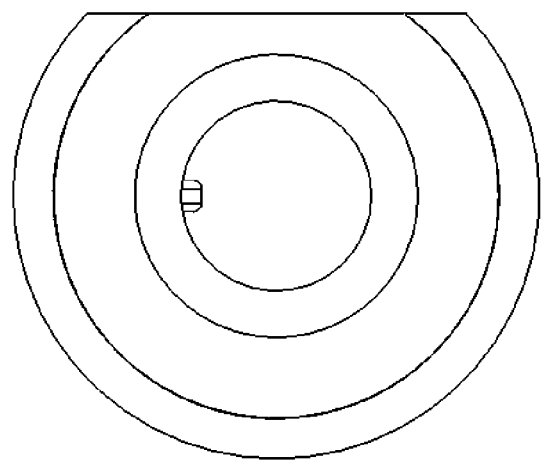
FIG. 4E is a proximal view of an electrosurgical surgical blade and connector assembly in accordance with a preferred embodiment of the present invention.

An assembly 400 of a surgical blade 200 in accordance with a preferred embodiment of the present invention is shown in FIGS. 4A-4E. The electrode or blade 200 has elongated proximal portion 210 and a paddle or blade distal portion 220.

The connector 500 and blade 200 may be formed from the same or different materials. For example, the connector 500 may be nickel-plated brass and the blade coated stainless steel. Other materials such as tungsten may be used. The connector 500 is at the proximal end of the blade 200. The proximal portion 210 of the electrode is connected to the distal end 514 of the connector 500 at the opening 550 and extends from the distal end 514 of the connector 500.

Figure 5A:
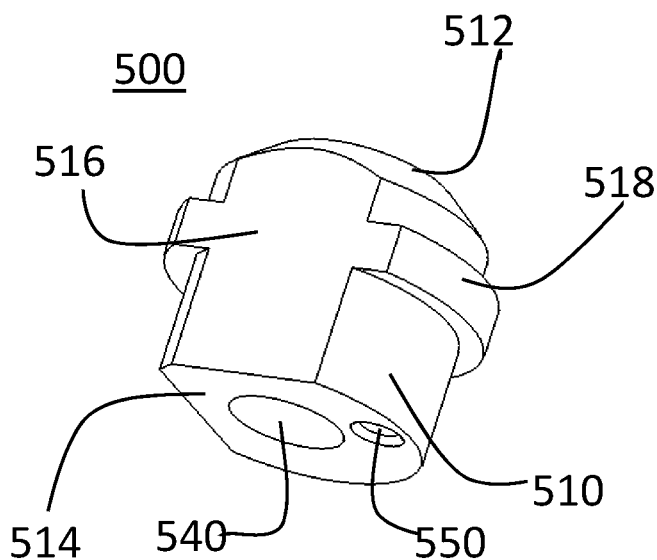
FIG. 5A is a perspective view of a connector for an electrosurgical surgical blade in accordance with a preferred embodiment of the present invention.
Figure 5B:
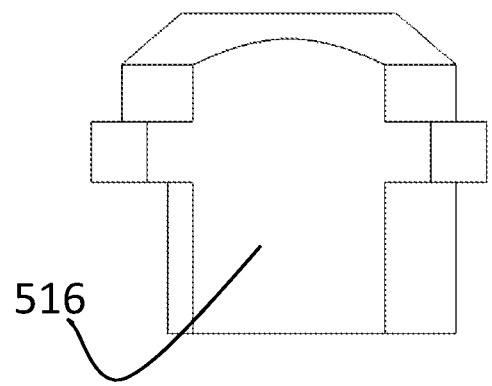
FIG. 5B is a first side view of a connector for an electrosurgical surgical blade in accordance with a preferred embodiment of the present invention.
Figure 5C:
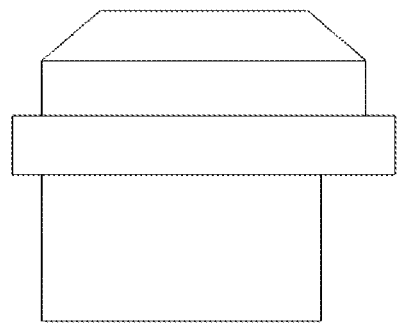
FIG. 5C is a second side view of a connector for an electrosurgical surgical blade in accordance with a preferred embodiment of the present invention.
Figure 5D:
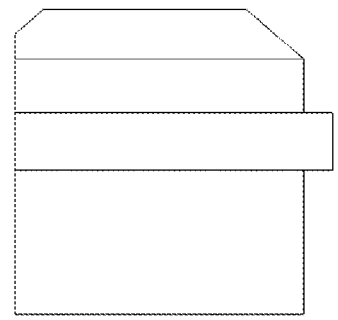
FIG. 5D is a front view of a connector for an electrosurgical surgical blade in accordance with a preferred embodiment of the present invention.
Figure 5E:
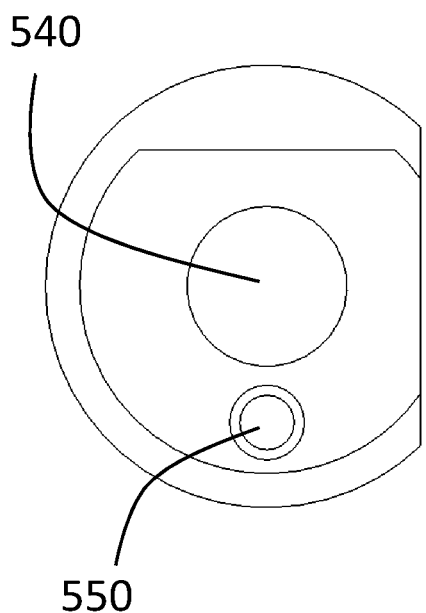
FIG. 5E is a bottom view of a connector for an electrosurgical surgical blade in accordance with a preferred embodiment of the present invention.
Figure 5F:
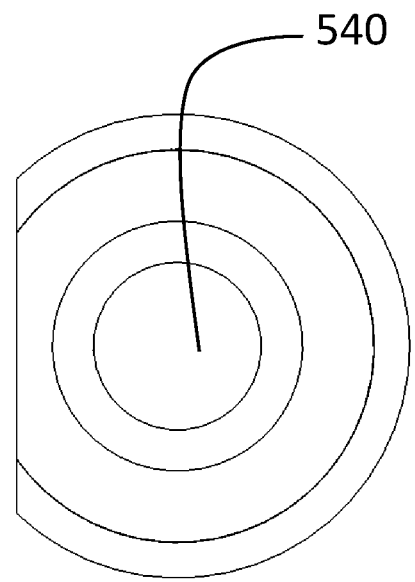
FIG. 5F is a top view of a connector for an electrosurgical surgical blade in accordance with a preferred embodiment of the present invention.
Figure 5G:
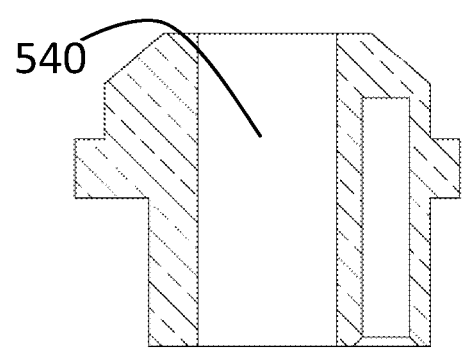
FIG. 5G is a cross-sectional side view of a connector for an electrosurgical surgical blade in accordance with a preferred embodiment of the present invention.

A metal connector 500 for a surgical blade in accordance with a preferred embodiment of the present invention is shown in FIGS. 5A-5G. The connector 500 has a connector body 510 having a beveled or rounded proximal end 512 and a distal end 514. The connector may generally be cylindrical in shape but may have a flat portion 516 for alignment with an electrosurgical hand piece. The body 510 has a channel 540 extending through it and a ridge, shoulder or flange 518.

When assembled with the housing 100 and the blade 200, the rounded or beveled portion 512 of the connector 500 provides a conductive surface for making a connection to connector (not shown) that in turn is connected to an electrosurgical generator (not shown). When assembled with the housing 100, the channel 540 in the connector aligns with the channel 170 in the housing to allow gas to flow through the channel 540 in the connector 500 and into the channel 170 in the housing. In alternative embodiments, the proximal portion 210 of the blade 200 further may have a bend to allow for alignment of the channels in the connector 500 and the housing 100.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An attachment for an electrosurgical hand piece of a gas-assisted electrosurgical device comprising:
   an elongated housing, said housing comprising:
      an elongated body having a channel within it;
      a proximal portion having a plurality of arms extending therefrom with each of said plurality of arms having an outward extending flange for securing said attachment to an electrosurgical hand piece;
   an electrosurgical blade comprising:
      a conductive member comprising a flat distal portion and a flat proximal end portion, said flat distal portion having a width greater than a width of said flat proximal end portion, the width of said distal portion being at least three times a thickness of the distal portion; and
      a coating on at least a portion of said conductive member;
   a conductive connector for connecting said conductive member to a conductor in an electrosurgical hand piece, wherein said connector comprises:
      a connector body;
      a channel within the connector body; and
      a slot off-center in a distal face of said connector body for receiving said proximal portion of said conductive member wherein a proximal end of said conductive member is secured in said slot; and
   a spacer support in said housing for supporting said flat distal portion of said conductive member, wherein said flat distal portion of said conductive member is centered in a distal end of said channel in said elongated body.

2. An attachment for a gas-assisted electrosurgical device according to claim 1, wherein said conductive member comprises one of stainless steel and tungsten.

3. An attachment for a gas-assisted electrosurgical device according to claim 1, further comprising a ceramic tip at a distal end of said housing, wherein said ceramic tip surrounds part of said distal portion of said conductive member and said ceramic tip has a proximal portion within said channel in said housing and a distal portion extending out of said channel in said housing.

4. An attachment for a gas-assisted electrosurgical device according to claim 1, wherein said distal portion of said conductive member has a rounded tip.

5. An attachment for a gas-assisted electrosurgical device according to claim 1, further comprising a support member within said channel in said housing body for supporting said conductive member within said housing.

6. An attachment for a gas-assisted electrosurgical device according to claim 1, further comprising a connector for connecting said attachment member to an electrosurgical hand piece.

7. An attachment for a gas-assisted electrosurgical device according to claim 1, wherein said connector body has a flat side for aligning said connector with said housing.

8. An attachment for a gas-assisted electrosurgical device according to claim 1, wherein said connector body is cylindrical in form and said slot for receiving said proximal end of said conductive member is off center in said cylindrical connector body.

9. An attachment for a gas-assisted electrosurgical device according to claim 1, wherein said channel in said connector body runs along a central axis of conductor body.

10. An attachment for a gas-assisted electrosurgical device according to claim 7, wherein said width of said distal portion of said conductive member is parallel to said flat side of said connector.

11. An attachment for an electrosurgical hand piece of a gas-assisted electrosurgical device comprising:
 a housing, said housing comprising:
  an elongated body having a channel within it;
  a proximal portion for securing said attachment to an electrosurgical hand piece;
 an electrode comprising:
  an elongated conductive member comprising:
   a flat distal portion and an elongated flat proximal end portion, said flat distal portion having a width greater than a width of said proximal portion, the width of said distal portion being at least three times a thickness of the distal portion; and
   a coating on at least a portion of said conductive member;
  a conductive connector for connecting said elongated conductive member to a conductor in an electrosurgical hand piece, wherein said conductive connector comprises:
   a connector body;
   a channel within the connector body; and
   an opening in a distal face of said connector body for receiving said proximal portion of said conductive member wherein a proximal end of said conductive member is secured in said opening; and
 a spacer support in said housing for supporting said flat distal portion of said conductive member, wherein said flat distal portion of said conductive member is centered in a distal end of said channel in said elongated body.

* * * * *